United States Patent
Versteyhe

(10) Patent No.: US 9,845,863 B2
(45) Date of Patent: Dec. 19, 2017

(54) MONITORING AND PROGNOSTIC SYSTEM AND METHOD FOR DETERMINING A REMAINING USEFUL LIFE OF LUBRICANT IN WET CLUTCH TRANSMISSIONS

(71) Applicant: DANA LIMITED, Maumee, OH (US)

(72) Inventor: Mark R. J. Versteyhe, Oostkamp (BE)

(73) Assignee: Dana Limited, Maumee, OH (US)

(*) Notice: Subject to any disclaimer, the term of this patent is extended or adjusted under 35 U.S.C. 154(b) by 87 days.

(21) Appl. No.: 14/392,089

(22) PCT Filed: Apr. 9, 2014

(86) PCT No.: PCT/US2014/033463
§ 371 (c)(1),
(2) Date: Sep. 28, 2015

(87) PCT Pub. No.: WO2014/169019
PCT Pub. Date: Oct. 16, 2014

(65) Prior Publication Data
US 2016/0053884 A1    Feb. 25, 2016

Related U.S. Application Data

(60) Provisional application No. 61/811,564, filed on Apr. 12, 2013.

(51) Int. Cl.
*F16H 57/00* (2012.01)
*G01N 33/00* (2006.01)
(Continued)

(52) U.S. Cl.
CPC ..... *F16H 57/0405* (2013.01); *G01N 33/2888* (2013.01)

(58) Field of Classification Search
None
See application file for complete search history.

(56) References Cited

U.S. PATENT DOCUMENTS 4,796,204 A    1/1989    Inoue
5,050,451 A *  9/1991    Hussain ............... B60W 10/06
                                                     477/120
(Continued)

OTHER PUBLICATIONS

Noria Corporation; A Comprehensive Look at the Acid Number Test; Practicing Oil Analysis; Jul. 2007; 9 pages.
(Continued)

*Primary Examiner* — Matthew G Marini
*Assistant Examiner* — Ruben Parco, Jr.
(74) *Attorney, Agent, or Firm* — Marshall & Melhorn, LLC

(57) ABSTRACT

A system and a method for monitoring a lubricant in a transmission are provided. The system comprises a first speed sensor, a temperature sensor, and a processing unit. The first speed sensor is positioned adjacent a first clutch, which forms a portion of the transmission. The first speed sensor is configured to detect a rotational difference between portions of the first clutch. The temperature sensor is disposed within the transmission. The temperature sensor is configured to measure a temperature of the lubricant. The processing unit is in communication with the first speed sensor and the temperature sensor. In response to information from the first speed sensor and the temperature sensor, the processing unit determines a condition of the lubricant used in the transmission.

18 Claims, 2 Drawing Sheets

(51) Int. Cl.
  *F16H 57/04* (2010.01)
  *G01N 33/28* (2006.01)

(56) References Cited

U.S. PATENT DOCUMENTS

| | | | |
|---|---|---|---|
| 5,060,156 A | 10/1991 | Vajgart et al. | |
| 5,530,647 A | 6/1996 | Sem et al. | |
| 5,633,796 A | 5/1997 | Cullen et al. | |
| 8,050,814 B2 | 11/2011 | Rains et al. | |
| 2004/0107055 A1* | 6/2004 | Kolosov | G01N 29/036 |
| | | | 702/25 |
| 2006/0052218 A1* | 3/2006 | Stengel | F16D 48/062 |
| | | | 477/166 |
| 2008/0156127 A1* | 7/2008 | Nicklass | F16H 3/006 |
| | | | 74/333 |
| 2012/0080286 A1* | 4/2012 | Kasuya | B60K 6/40 |
| | | | 192/113.3 |
| 2012/0303230 A1* | 11/2012 | Qiao | G01N 33/2888 |
| | | | 701/59 |
| 2015/0191174 A1* | 7/2015 | Ishikawa | F02D 41/022 |
| | | | 477/54 |

OTHER PUBLICATIONS

European Patent Office; International Search Report and Written Opinion; dated Jul. 9, 2015; 10 pages; Rijswijk, Netherlands.

\* cited by examiner

MONITORING AND PROGNOSTIC SYSTEM AND METHOD FOR DETERMINING A REMAINING USEFUL LIFE OF LUBRICANT IN WET CLUTCH TRANSMISSIONS

RELATED APPLICATIONS

The present application claims the benefit of U.S. Provisional Application No. 61/811,564 filed on Apr. 12, 2013, which is incorporated herein in its entirety by reference.

FIELD OF THE INVENTION

The present invention relates lubricant monitoring, and more specifically to a system and a method for monitoring a lubricant in a transmission.

BACKGROUND OF THE INVENTION

A shifting wet clutch incorporated into a vehicle typically uses an automatic transmission fluid to lubricate and facilitate operation of the shifting wet clutch or other transmission components. Through use of the transmission and operation of the shifting wet clutch, the automatic transmission fluid progressively degrades. A maintenance strategy for vehicles equipped with the shifting wet clutch includes replacement of the automatic transmission fluid upon degradation. However, as the degradation process of the automatic transmission fluid is very complex, determining when the automatic transmission fluid should be replaced is difficult, and complicates the maintenance strategy of the vehicle. A monitoring and prognostics system for determining when the automatic transmission fluid should be replaced without significantly increasing a cost of the vehicle the monitoring and prognostics system is incorporated in would be advantageous.

The degradation process of the automatic transmission fluid comprises a plurality of separate processes. Non-limiting examples of the plurality of separate processes are oxidation, thermal breakdown, microdieseling, electrostatic spark discharge, additive depletion, water contamination, and excessive shear load. An example of the degradation process of an automatic transmission fluid is illustrated in FIG. 1.

Oxidation is a chemical process caused by exposure to oxygen. Besides an oxygen concentration in a surrounding environment, oxidation is also influenced by other factors, such as a temperature of the surrounding environment and a presence of a catalyst which may increase a rate of oxidation. Non-limiting examples of the catalyst are water and wear metal ions.

Oxidation is the most predominant process that contributes to the degradation process. Oxidation of the automatic transmission fluid results in an increase in a viscosity of the automatic transmission fluid, formation of a varnish, sludge and sediment within the automatic transmission fluid, a depletion of additives in the automatic transmission fluid, a breakdown of a base oil of the automatic transmission fluid, a plugging of a filter used with the automatic transmission fluid, a loss in foaming properties of the automatic transmission fluid, an increase in an acid number of the automatic transmission fluid, an ability of rust to form on the components of the transmission, and a corrosion of the components of the transmission.

Thermal breakdown can cause the automatic transmission fluid to vaporize or the automatic transmission fluid to decompose. Vaporization or decomposition can cause additives to be removed from the automatic transmission fluid, resulting in a loss of function of the automatic transmission fluid. Further, as a result of the additives being removed from the automatic transmission fluid, the viscosity of the automatic transmission fluid may increase. One source of thermal breakdown is from friction which occurs between the moving parts of the transmission. Friction may cause the automatic transmission fluid to heat up above a recommended stable temperature. As a non-limiting example, the recommended stable temperature may be a flash point of the automatic transmission fluid.

Thermal breakdown occurs when a temperature of the automatic transmission fluid greatly exceeds the recommended stable temperature of the automatic transmission fluid, larger molecules of the automatic transmission fluid will break apart into smaller molecules. Thermal breakdown can trigger side reactions, such as inducing polymerization, producing gaseous by-products, destroying additives and generating insoluble by-products. In some cases, the viscosity of the automatic transmission fluid may decrease due to thermal breakdown.

Microdieseling, which may also be referred to as pressure-induced thermal degradation, is a process in which an air bubble transitions from a low-pressure to a high-pressure zone, resulting in adiabatic compression. Such a process produces localized temperatures in excess of 1,000° C., which results in a formation of carbonaceous byproducts and accelerated degradation of the automatic transmission fluid.

Electrostatic spark discharge can occur when clean and dry automatic transmission fluid rapidly flows through tight clearances in the transmission. Internal friction in the automatic transmission fluid generates static electricity which can accumulate until a spark occurs. Such a spark occurs at an estimated temperature of between 10,000° C. and 20,000° C.

Due to a natural consequence of aging, some additives of the automatic transmission fluid are depleted. Monitoring additive levels is important not only to assess the health of the automatic transmission fluid, but it also may provide information related to specific degradation mechanisms.

Water contamination in the automatic transmission fluid occurs when water is dissolved in the automatic transmission fluid. When this occurs, water molecules are dispersed evenly within the automatic transmission fluid. When a maximum level of dissolved water in the automatic transmission fluid is reached, microscopic water droplets are uniformly distributed in the automatic transmission fluid to form an emulsion. When additional water is added to the emulsion, the two components will become separated, which results in free water in the automatic transmission fluid Effects of water in the automatic transmission fluid include rust and corrosion to the components of the transmission, erosion to the components of the transmission, water etching to the components of the transmission, and hydrogen embrittlement of the components of the components of the transmission. In addition water can also accelerate the oxidation process, deplete oxidation inhibitors and demulsifiers added to the automatic transmission fluid, precipitate additives added to the automatic transmission fluid and compete with polar additives such as friction modifiers for components of the transmission.

Excessive shear load is another process that contributes to the degradation process of the automatic transmission fluid. Excessive shear load can scissor a molecular chain of viscosity modifiers of the automatic transmission fluid, resulting in a permanent viscosity loss of the automatic transmission fluid.

Some indicators revealing quality of the automatic transmission fluid after use for long periods of time have been reported. These indicators can be classified as follows:

When the automatic transmission fluid is clear and bright, this indicates that there are no deposits, and the automatic transmission fluid is still in good condition. When automatic transmission fluid becomes darker in color, such color generally indicates that the automatic transmission fluid has been in use for a long period of time and/or that some oxidation of the automatic transmission fluid has occurred.

The viscosity is a measure of a resistance to flow, or how thick or thin the automatic transmission fluid is. The viscosity of automatic transmission fluid is an important property of the automatic transmission fluid which is indicative of performance. A decrease in the viscosity of the automatic transmission fluid can be caused by an admixture with a lower viscosity oil, a breakdown of polymeric compounds of the fluid viscosity index from excessive shear loads or thermal breakdown. An increase of the viscosity of the automatic transmission fluid can be caused by an admixture with a higher viscosity oil, contamination of the automatic transmission fluid with heavy fuel, combustion products, or products from incomplete combustion (such as soot, solids, coolant and water) or oxidation.

The ability of the automatic transmission fluid to combat effects of acid formation is indicated by a total base number (TBN) of the automatic transmission fluid. Acid is typically formed during the oxidation process. A low TBN can indicate an admixture with a lower TBN oil, or depletion of additives. Such depletion of additives may indicate that the automatic transmission fluid is exposed to severe conditions such as high sulphur fuel, over-extended oil drain, inappropriate transmission design, and harsh operating conditions. A high TBN can indicate an admixture with a higher TBN oil, a decomposition of alkaline additives of the automatic transmission fluid by high temperature, and a stripping of light ends from the automatic transmission fluid.

Acidity of the automatic transmission fluid is an indicator of serviceability. Acidity of the automatic transmission fluid increases with oxidation and the introduction of combustion byproducts. Acidity of the automatic transmission fluid may be measured using a total acid number (TAN) of the automatic transmission fluid. A lower TAN may indicate an admixture of the automatic transmission fluid with a lower TAN oil, depletion of additives contributing to the TAN of the automatic transmission fluid, and contamination of the automatic transmission fluid with alkaline oils or other materials (such as cleaning agents, for example). A higher TAN may be caused by an admixture of the automatic transmission fluid with a higher TAN oil, oxidation of the automatic transmission fluid, contamination of the automatic transmission fluid with acid combustion products, a thermal breakdown of certain additives, and contamination of the automatic transmission fluid with acidic materials (such as cleaning agents, for example). The higher TAN of the automatic transmission fluid can produce corrosion of the components of the transmission, thickening of the automatic transmission fluid, formation of deposits within the transmission, and an accelerated wear of the components of the transmission. It is understood that the TBN and the TAN are complementary. Further, the TAN and a viscosity of an automatic transmission fluid may vary over a course of time, as can be seen in FIGS. 3A-3C, which have been based on information from "A comprehensive look at the acid number test" by the Noria Corporation. *Practicing Oil Analysis,* 2007: 1-9.

Causes of water presence in the automatic transmission fluid include condensation, low operating temperatures of an engine, leakage of other components into the transmission, ingress into the transmission, water present in new automatic transmission fluid, and a mixing of the automatic transmission fluid with combustion gases. The effects of water in the automatic transmission fluid are rust and corrosion of the components of the transmission, a sludge formation within the transmission, an increase in oxidation of the automatic transmission fluid, a decrease in fatigue life (typically of bearings and gears of the transmission), an increased wear of the components of the transmission, a reduced additive protection, and plugging of the filter of the automatic transmission fluid.

Solids in the automatic transmission fluid can come from many sources, but common causes include wear debris particles from the friction plates, gears, and bearings of the transmission, products of the oxidation process, and ingress of environmental products into the transmission (such as sand and soil, for example). The effects of high solids content are a thickening of the automatic transmission fluid, abrasive wear of the components of the transmission, formation of deposits with the transmission, and plugging of the filter of the automatic transmission fluid.

As mentioned hereinabove, the degradation process which occurs in the automatic transmission fluid is very complex. Many factors are involved in determining the degradation of the automatic transmission fluid, such as an operating condition and an environment of the transmission. However, it is known that the oxidation process is the major mechanism causing degradation of the automatic transmission fluid. As a result of the oxidation process, the automatic transmission fluid becomes more acidic and more viscous. As a result, the total acid number and the viscosity are two metrics that may be used to determine a condition of the automatic transmission fluid.

It would be advantageous to develop a system and a method for determining a remaining useful life of lubricant in a wet clutch transmission that is accurate and is based on data from sensors which are available in the transmission without significantly increasing a cost of the transmission or a vehicle the transmission is incorporated in.

SUMMARY OF THE INVENTION

Presently provided by the invention, a system and a method for determining a remaining useful life of lubricant in a wet clutch transmission that is accurate and is based on data from sensors which are available in the transmission without significantly increasing a cost of the transmission or a vehicle the transmission is incorporated in, has surprisingly been discovered.

In one embodiment, the present invention is directed to a system and a method for monitoring a lubricant in a transmission. The system comprises a first speed sensor, a temperature sensor, and a processing unit. The first speed sensor is positioned adjacent a first clutch, which forms a portion of the transmission. The first speed sensor is configured to detect a rotational difference between portions of the first clutch. The temperature sensor is disposed within the transmission. The temperature sensor is configured to measure a temperature of the lubricant. The processing unit is in communication with the first speed sensor and the temperature sensor. In response to information from the first speed sensor and the temperature sensor, the processing unit determines a condition of the lubricant used in the transmission.

In another embodiment, the present invention is directed to a method for monitoring a lubricant in a transmission. The steps of the method comprise providing a first speed sensor positioned adjacent a first clutch forming a portion of the transmission; providing a temperature sensor disposed within the transmission; providing a processing unit in communication with the first speed sensor and the temperature sensor; detecting a rotational difference between portions of the first clutch using the first speed sensor; measuring a temperature of the lubricant using the temperature sensor; and determining a condition of the lubricant used in the transmission using the processing unit using the information from the first speed sensor and the temperature sensor.

In yet another embodiment, the present invention is directed to a method for monitoring a lubricant in a transmission. The steps of the method comprise providing a first speed sensor positioned adjacent a first clutch forming a portion of the transmission; providing a second speed sensor positioned adjacent a second clutch forming a portion of the transmission; providing a temperature sensor disposed within the transmission; providing a processing unit in communication with the first speed sensor, the second speed sensor, and the temperature sensor; detecting a rotational difference between portions of the first clutch using the first speed sensor; detecting a rotational difference between portions of the second clutch using the second speed sensor; measuring a temperature of the lubricant using the temperature sensor; and determining a viscosity of the lubricant used in the transmission using the processing unit using the information from the first speed sensor, the second speed sensor, and the temperature sensor.

Various aspects of this invention will become apparent to those skilled in the art from the following detailed description of the preferred embodiment, when read in light of the accompanying drawings.

BRIEF DESCRIPTION OF THE DRAWINGS

The above, as well as other advantages of the present invention will become readily apparent to those skilled in the art from the following detailed description when considered in the light of the accompanying drawings in which.

DETAILED DESCRIPTION OF THE PREFERRED EMBODIMENTS

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined herein. Hence, specific dimensions, directions or other physical characteristics relating to the embodiments disclosed are not to be considered as limiting, unless expressly stated otherwise.

Figure 1:
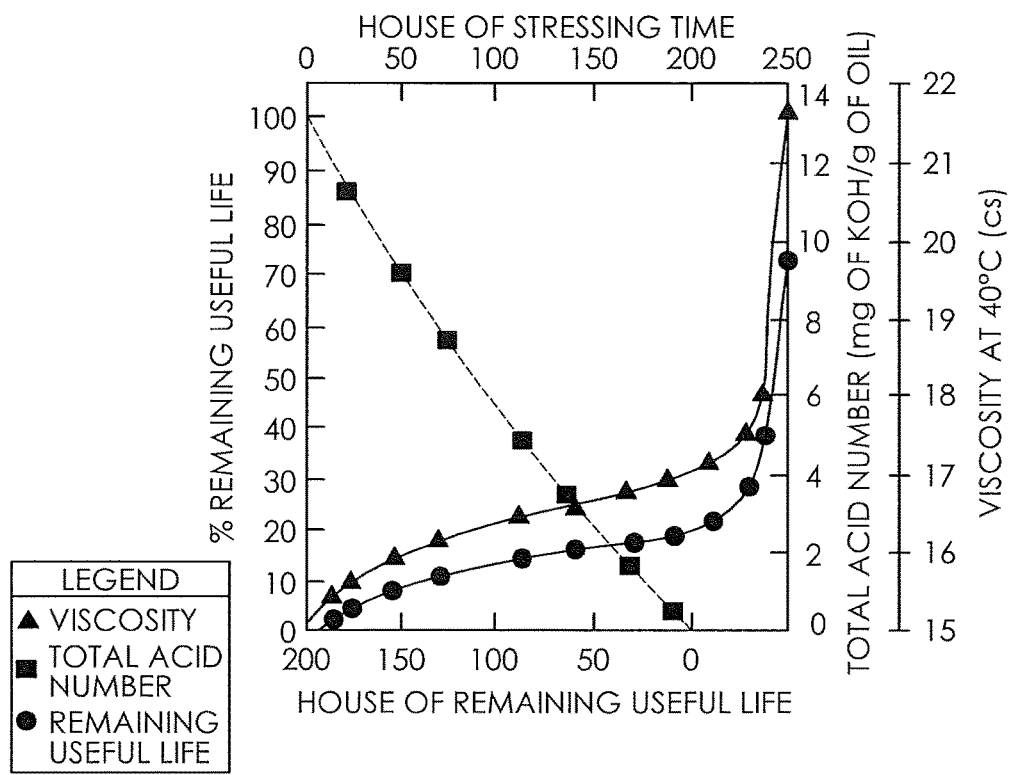
FIG. 1 is a chart illustrating a degradation process of an automatic transmission fluid.
Figure 2:
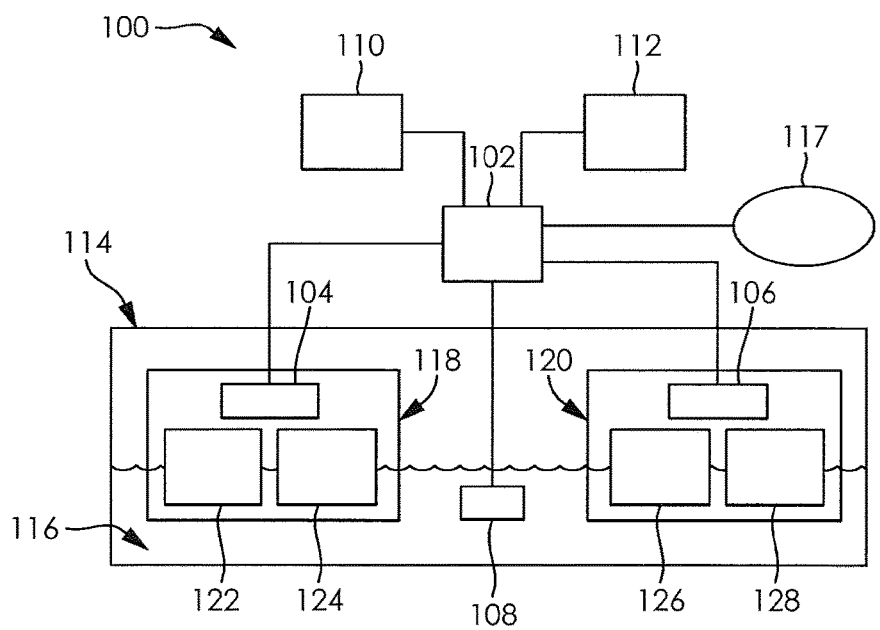
FIG. 2 is a schematic illustration of a system for monitoring a lubricant in a transmission according to an embodiment of the invention.

FIG. 2 illustrates a system 100 for determining a remaining useful life of lubricant in a wet clutch transmission according to an embodiment of the invention. The system 100 comprises a processing unit 102, a first speed sensor 104, a second speed sensor 106, a temperature sensor 108, a storage device 110, and a user interface 112. The first speed sensor 104, the second speed sensor 106, and the temperature sensor 108 sense information regarding an operating condition of a transmission 114. In response to conditions detected and determined by the system 100 using the sensors 104, 106, 108, the system 100 notifies an operator of a vehicle (not shown) incorporating the system 100 regarding a condition of a lubricant 116 (such as an automatic transmission fluid, for example) used in the transmission 114 or transmits information to a central network 117.

The transmission 114 forms a portion of a driveline (not shown) for a vehicle incorporating the system 100. The transmission 114, which is shown schematically in FIG. 2, is an automatic transmission including at least a first clutch 118 and a second clutch 120; however, it is understood that the transmission 114 may be any type of transmission that includes at least two clutching devices.

The first clutch 118 is a wet plate style clutch which may be variably engaged; however, it is understood that the first clutch 118 may be another type of engagement device. The first clutch 118 comprises a driven portion 122 and a non-driven portion 124. The first clutch 118 may be placed in an engaged position, a disengaged position, or a slipping condition. When the first clutch 118 is placed in the engaged position, the driven portion 122 is drivingly engaged with the non-driven portion 124, and no relative movement therebetween occurs. When the first clutch 118 is placed in the disengaged position, the driven portion 122 is not drivingly engaged with the non-driven portion 124, allowing either the driven portion 122 or the non-driven portion 124 to rotate with respect to one another without affecting a remaining portion of the first clutch 118.

The first speed sensor 104 is a sensor in data communication with the processing unit 102. The first speed sensor 104 is positioned adjacent the driven portion 122 and the non-driven portion 124. The first speed sensor 104 is configured to detect a rotational difference between the driven portion 122 and the non-driven portion 124, which is communicated to the processing unit 102.

The second clutch 120 is a wet plate style clutch which may be variably engaged; however, it is understood that the second clutch 120 may be another type of engagement device. The second clutch 120 comprises a driven portion 126 and a non-driven portion 128. The second clutch 120 may be placed in an engaged position, a disengaged position, or a slipping condition. When the second clutch 120 is placed in the engaged position, the driven portion 126 is drivingly engaged with the non-driven portion 128, and no relative movement therebetween occurs. When the second clutch 120 is placed in the disengaged position, the driven portion 126 is not drivingly engaged with the non-driven portion 128, allowing either the driven portion 126 or the non-driven portion 128 to rotate with respect to one another without affecting a remaining portion of the second clutch 120.

The second speed sensor 106 is a sensor in data communication with the processing unit 102. The second speed sensor 106 is positioned adjacent the driven portion 126 and the non-driven portion 128. The second speed sensor 104 is configured to detect a rotational difference between the driven portion 126 and the non-driven portion 128, which is communicated to the processing unit 102.

The temperature sensor 108 is a sensor in data communication with the processing unit 102. The temperature sensor 108 is positioned within the transmission 114 and is in contact with the lubricant 116. The temperature sensor 108 is configured to detect a temperature of the lubricant 116 within the transmission 114, which is communicated to the processing unit 102.

The processing unit 102 is a computing device forming a portion of the controller (not shown) of the vehicle. The processing unit 102 executes a series of instructions in response to the data received from the first speed sensor 104, the second speed sensor 106, and the temperature sensor 108. The processing unit 102 may also execute a series of instructions in response to a data received from additional sensors to facilitate operation of the vehicle. In response to data received from the first speed sensor 104, the second speed sensor 106, and the temperature sensor 108, the processing unit 102 may access information on the storage device 110, change information on the storage device 110, transmit information to the user interface 112, or transmit information to the central network 117. It is understood that the series of instructions executed by the processing unit 102 may be stored on the storage device 110 or an additional storage device (not shown).

The storage device 110 is in communication with the processing unit 102. The storage device 110 may be an EEPROM chip, a flash memory chip, or another form of non-volatile computer memory. As mentioned hereinabove, the processing unit 102 may access information on the storage device 110 or change information on the storage device 110. Information stored on the storage device 110 may include reference data or a series of instructions to be executed by the processing unit 102.

The user interface 112 is a device that facilitates communication between the processing unit 102 and the operator of the vehicle incorporating the system 100. The user interface may be a lighting device, an audio device, or may form a portion of a computerized user interface (not shown). In response to information received from the processing unit 102, the user interface 112 is activated in a manner to alert the operator of the vehicle regarding a condition of the lubricant 116 used in the transmission 114.

The central network 117 is a communication platform the processing unit 102 is in communication with. The central network 117 comprises at least one computing device (not shown) which facilitates a transfer, storage, or manipulation of data received from the central network 117. Further, the central network 117 may transmit information to the processing unit 102 regarding an operation of the vehicle. As a non-limiting example, the central network 117 may be a fleet management system.

In use, the system 100 notifies an operator of the vehicle incorporating the system 100 regarding a condition of the lubricant 116 used in the transmission 114 or transmits information to the central network 117 in response to conditions detected and determined by the system 100 using the sensors 104, 106, 108.

FIG. 2 illustrates a working principle of the system 100 for monitoring and prognostics. Information from the speed sensors 104, 106 and the temperature sensor 108 of each of the clutches 118, 120 placed in the disengaged position are sent to the processing unit 102. Further, the processing unit 102 considers a specification of the lubricant 116 and an amount of time since the lubricant 116 has been changed. The processing unit 102 then calculates and transmits information regarding a health of the lubricant 116, a remaining useful life of the lubricant 116, and an indication of a next estimated change of the lubricant 116 to the user interface 112. It is understood that the user interface 112 may be any kind of interface (such as one shown on an LCD screen or an application on a mobile wireless device, for example).

Next, the processing unit 102 (or another processing unit in communication with the processing unit 102) may transmit the information displayed on the user interface 112 to the central network 117. On the central network 117, such information may be used by a fleet management system to facilitate dispatching vehicles, to schedule maintenance of the vehicle, and to follow change over a course of time of the lubricant 116.

The speed sensors 104, 106 are used to identify a change of the relative velocity signals between the driven portions 122, 126 and the non-driven portions 124, 128 of the clutches 118, 120 when placed in the disengaged position (prior to applying pressure at high velocity), wherein a resulting friction torque is mainly controlled by the properties of lubricant 116 (such as a viscosity of the lubricant 116, for example). When one of the clutches 118, 120 is fully disengaged, the non-driven portions 124, 128 of one of the clutches 118, 120 may turn as a result of friction between the driven portions 122, 126 of the clutches 118, 120 and the lubricant 116. A speed differential between each of the driven portions 122, 126 and the non-driven portions 124, 128 of each of the clutches 118, 120 in the disengaged position allows information to be determined regarding a viscosity of the lubricant 116. For example, when a viscosity of the lubricant 116 is low, a resulting relative velocity signal between the driven portions 122, 126 and the non-driven portions 124, 128 of each of the clutches 118, 120 in the disengaged position tends to be high. Conversely and for example, when a viscosity of the lubricant 116 is high, a resulting relative velocity signal between the driven portions 122, 126 and the non-driven portions 124, 128 of each of the clutches 118, 120 in the disengaged position tends to be low. Since a resulting friction torque is greatly influenced by a temperature of the lubricant 116, the temperature sensor 108 is used to correct an effect of the temperature of the lubricant 116 on the relative velocity signal.

The speed and temperature information from the clutches 118, 120 in the disengaged position can be compared to ensure a better accuracy and reliability of the system 100 for monitoring and prognostics. While FIG. 2 only illustrates the system 100 including two clutches 118, 120, it is understood that the system 100 may include additional clutches.

Figure 3A:
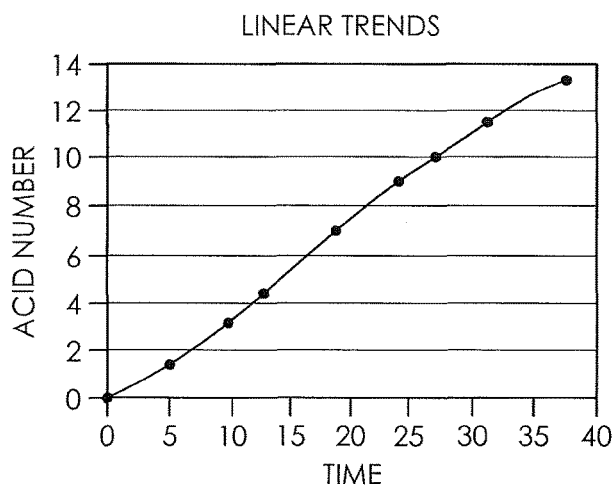
FIG. 3A is a chart illustrating a linear relationship of a total acid number of an automatic transmission fluid over a course of time.
Figure 3B:
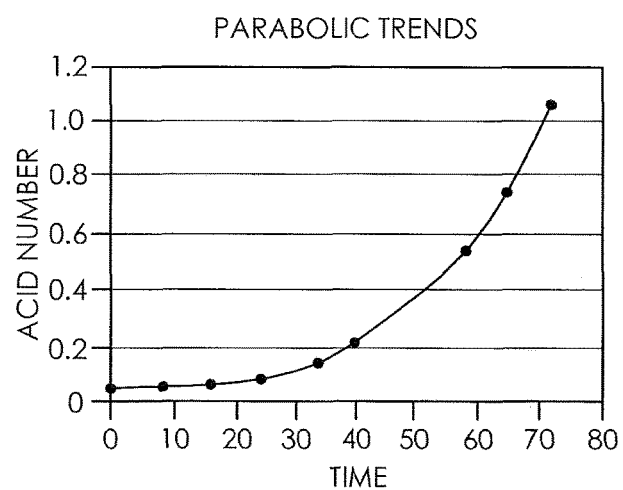
FIG. 3B is a chart illustrating a parabolic relationship of a total acid number of an automatic transmission fluid over a course of time.
Figure 3C:
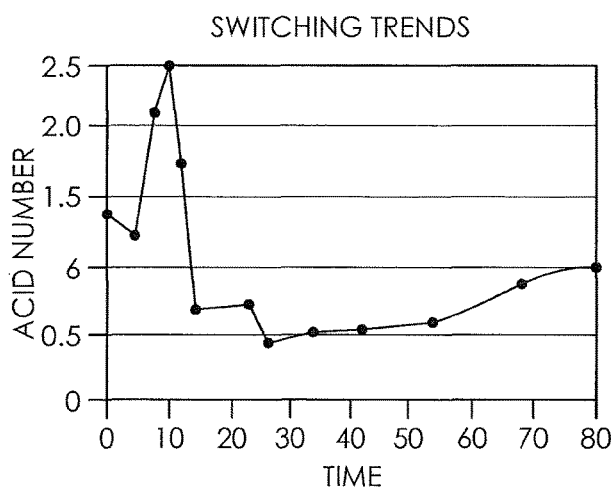
FIG. 3C is a chart illustrating an erratic relationship of a total acid number of an automatic transmission fluid over a course of time.

As mentioned hereinabove, oxidation is the main degradation mechanism of the automatic transmission fluid (such as the lubricant 116), it is therefore important to understand how the TAN and the viscosity of the automatic transmission fluid change over a course of time. As commercially available automatic transmission fluids may have different additives, a TAN and a viscosity over a course of time may differ as can be seen in FIGS. 3A-3C. As shown in FIGS. 3A-3C, such a change over a course of time may be a linear, parabolic or erratic relationship, depending on a composition of the automatic transmission fluid.

Accelerated oxidation tests may determine a behavior of an automatic transmission fluid used in a transmission (such as the transmission 114). Furthermore, if a change in viscosity is correlated to the change of TAN, as shown in FIG.

1, merely monitoring the viscosity of the lubricant 116 using the speed sensors 104, 106 is sufficient to determine a quality of the lubricant 116.

It is further understood that a good knowledge and a selection of an automatic transmission fluid is of paramount importance and that different behaviors have to be implemented in the system 100 for monitoring and prognostics. A function of the system 100 for monitoring and prognostics allows the operator of the vehicle incorporating the system 100 for monitoring and prognostics to select an automatic transmission fluid used with the vehicle.

The system 100 for monitoring and prognostics of the present invention has many advantages. The system 100 for monitoring and prognostics is simple to implement and cost effective as the system 100 uses existing sensors (the speed sensors 104, 106 and the temperature sensor 108, for example). The system 100 for monitoring and prognostics combines information from the speed sensors 104, 106 and the temperature sensor 108 of any of the clutches 118, 120 placed in a disengaged position to determine a viscosity of the lubricant 116. The system 100 for monitoring and prognostics includes a plurality of internal models which are used to determine a correlation between the viscosity and the oxidation of the lubricant 116 through a viscosity/TAN correlation. The system 100 for monitoring and prognostics includes a plurality of internal models that make a link between an oxidation of the lubricant 116 and a remaining useful life of the lubricant 116. The system 100 for monitoring and prognostics may be adapted for use with a variety of commercially available automatic transmission fluids. The system 100 for monitoring and prognostics transmits information regarding the lubricant 116 (the remaining useful life, for example) to the operator of the vehicle the system 100 is incorporated in. The system 100 for monitoring and prognostics provides a possibility to transfer information to the central network 117 so that such information may be used by the fleet management system.

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed is:

1. A system for monitoring a lubricant in a transmission, the system comprising:
    a first clutch comprising a driven portion and a non-driven portion forming a portion of the transmission;
    a first speed sensor positioned adjacent the first clutch, the first speed sensor configured to detect a rotational difference between the driven portion and the non-driven portion of the first clutch;
    a temperature sensor disposed within the transmission, the temperature sensor configured to measure a temperature of the lubricant; and
    a processing unit in communication with the first speed sensor and the temperature sensor,
    wherein in response to information from the first speed sensor and the temperature sensor, the processing unit determines a condition of the lubricant used in the transmission.

2. The system for monitoring the lubricant in the transmission according to claim 1, wherein the processing unit determines a viscosity of the lubricant used in the transmission in response to information from the first speed sensor and the temperature sensor.

3. The system for monitoring the lubricant in the transmission according to claim 2, wherein the processing unit determines a quality of the lubricant based on the viscosity of the lubricant.

4. The system for monitoring the lubricant in the transmission according to claim 1, further comprising a second clutch forming a portion of the transmission and a second speed sensor, the second speed sensor positioned adjacent the second clutch, the second speed sensor configured to detect a rotational difference between portions of the second clutch.

5. The system for monitoring the lubricant in the transmission according to claim 1, wherein the first speed sensor is configured to detect a rotational difference between the driven portion and the non-driven portion of the first clutch when the first clutch is placed in a disengaged position.

6. The system for monitoring the lubricant in the transmission according to claim 1, further comprising a storage device in communication with the processing unit, the storage device including at least one of reference data and a series of instructions to be executed by the processing unit.

7. The system for monitoring the lubricant in the transmission according to claim 1, further comprising a user interface in communication with the processing unit, the user interface facilitating communication between the processing unit and an operator of the transmission.

8. The system for monitoring the lubricant in the transmission according to claim 1, wherein the first clutch is a wet plate style clutch.

9. The system for monitoring the lubricant in the transmission according to claim 1, wherein the processing unit is in communication with a central network.

10. A method for monitoring a lubricant in a transmission, the steps of the method comprising:
    providing a first speed sensor positioned adjacent a first clutch forming a portion of the transmission, the first clutch comprising a driven portion and a non-driven portion;
    providing a temperature sensor disposed within the transmission;
    providing a processing unit in communication with the first speed sensor and the temperature sensor;
    detecting a rotational difference between the driven portion and the non-driven portion of the first clutch using the first speed sensor;
    measuring a temperature of the lubricant using the temperature sensor; and
    determining a condition of the lubricant used in the transmission using the processing unit using the information from the first speed sensor and the temperature sensor.

11. The method for monitoring the lubricant in the transmission according to claim 10, wherein the step of determining a condition of the lubricant used in the transmission using the processing unit determines a viscosity of the lubricant using the information from the first speed sensor and the temperature sensor.

12. The method for monitoring the lubricant in the transmission according to claim 11, wherein the step of determining a condition of the lubricant used in the transmission using the processing unit determines a quality of the lubricant based on the viscosity of the lubricant.

13. The method for monitoring the lubricant in the transmission according to claim 10, further providing a second speed sensor positioned adjacent a second clutch forming a portion of the transmission.

14. The method for monitoring the lubricant in the transmission according to claim 13, further comprising the step of detecting a rotational difference between portions of the second clutch using the second speed sensor.

15. The method for monitoring the lubricant in the transmission according to claim 10, wherein the first speed sensor is configured to detect a rotational difference between the driven portion and the non-driven portion of the first clutch when the first clutch is placed in a disengaged position.

16. The method for monitoring the lubricant in the transmission according to claim 10, further providing a storage device in communication with the processing unit, the storage device including at least one of reference data and a series of instructions to be executed by the processing unit.

17. The method for monitoring the lubricant in the transmission according to claim 10, further providing a user interface in communication with the processing unit, the user interface facilitating communication between the processing unit and an operator of the transmission.

18. A method for monitoring a lubricant in a transmission, the steps of the method comprising:

providing a first speed sensor positioned adjacent a first clutch forming a portion of the transmission;

providing a second speed sensor positioned adjacent a second clutch forming a portion of the transmission;

providing a temperature sensor disposed within the transmission;

providing a processing unit in communication with the first speed sensor, the second speed sensor, and the temperature sensor;

detecting a rotational difference between portions of the first clutch using the first speed sensor;

detecting a rotational difference between portions of the second clutch using the second speed sensor;

measuring a temperature of the lubricant using the temperature sensor; and determining a viscosity of the lubricant used in the transmission using the processing unit using the information from the first speed sensor, the second speed sensor, and the temperature sensor.

\* \* \* \* \*